US00PP11854P2

(12) United States Plant Patent
Fleming et al.

(10) Patent No.: US PP11,854 P2
(45) Date of Patent: May 1, 2001

(54) HIBISCUS PLANT NAMED 'PLUM CRAZY'

(75) Inventors: David W. Fleming; Gretchen A. Zwetzig, both of Lincoln, NE (US)

(73) Assignees: Fleming's Flower Fields, Inc.; David Fleming; Gretchen Zwetzig, all of Lincoln, NE (US)

( * ) Notice: Subject to any disclaimer, the term of this patent is extended or adjusted under 35 U.S.C. 154(b) by 0 days.

(21) Appl. No.: 09/289,835

(22) Filed: Apr. 12, 1999

(51) Int. Cl.[7] ..... A01H 5/00

(52) U.S. Cl. ..... Plt./257

(58) Field of Search ..... Plt./257

*Primary Examiner*—Bruce R. Campell
*Assistant Examiner*—Wendy A. Baker

(57) ABSTRACT

A new and distinct cultivar of winter hardy hibiscus plant named 'Plum Crazy' is the result of a unique hybridization. This new and distinct cultivar is characterized primarily as to novelty by its extreme cold hardiness to Zone 4, its rich dark purple "maple-cut" leaves, its large, campanulate plum flowers with dark purple centers and purple streaking to the petal edges, its vigorous and uniform growth habit, and its floriferous nature from midsummer until frost.

2 Drawing Sheets

BACKGROUND OF THE NEW PLANT

The new plant of this invention is the result of a unique hybridization, with the breeding acheivement being evidenced in the outstanding combination of characteristics exhibited by this new and distinct hibiscus plant, which include:

(a) Refined and uniquely colored 3 to 5-lobed leaves with a "maple-cut" which have relatively smooth margins and an evenly distributed dark, plum-purple coloration that compliments the landscape:

(b) Shimmering dark purple buds that open into large, calithiform flowers that are well-posed on the plant and outstanding for their plum, thick-textured petals with deep, purple centers, which streak through venation to the edges of the petals;

(c) The plant being very floriferous with flowers that stay open at least one full day;

(d) The plant being medium-sized, but vigorous, with compact and uniform breaking action which gives it unique landscape utility; and (e) The plant being so hardy that it can consistently withstand winter temperatures of at least —30 degrees Fahrenheit.

SUMMARY OF THE INVENTION

'Plum Crazy' was the result of a 40-year breeding program. Its ancestry includes *Hibiscus moscheutos* and *Hibiscus coccineus*. More specifically, the plant resulted from crossing a Fleming unnamed seedling resulting from multiple crossings of *Hibiscus coccineus* and *Hibiscus moscheutos* with the self-pollinated progeny of 'Dahliatown Orchid' (not patented). The seedling which met all above named standards was selected.

This new plant first bloomed in the summer of 1970 and was selected by David Fleming and Gretchen Zwetzig on David Fleming's property in Lincoln, Nebr. Asexual propagation of the plant by cuttings and root division in Lincoln, Nebr., has shown that the unique and distinguishing features of the plant are faithfully transmitted from generation to generation and appear to be fixed.

Since its origin, the plant has bloomed from midsummer until frost, while exhibiting the above-mentioned distinctive charateristics. This hardy hibiscus plant contributes to the market with its sheer beauty, its compact growth habit, its great resistance to disease and insects, its stability through extremes in rain and drought, and its extreme hardiness.

BRIEF DESCRIPTION OF THE DRAWINGS

The flower, bud, foliage, and growth habit of the plant are shown in the attached illustrations.

More specifically, the first drawing shows a close-up of the bloom and foliage. The second drawing depicts the growth habit of the cultivar, from the ground up to the apex of the plant. The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color designations set forth by PLATE and number designations are in accordance with the *Dictionary of Color* (Maerz and Paul), while general color recitations are consistent with ordinary American color terminology.

'Plum Crazy' has not been observed under all possible environmental conditions. Its is to be understood that the phenotype may vary significantly with variations in environment such as temperature, light intensity, and day length, without, however any difference in genotype of the plant. The following botanical characteristics and observations are taken from a 7 to 8 year-old plant when grown under normal outdoor conditions in Lincoln, Nebr.

THE PLANT

Parentage:

*Seed parent*.—The self-pollinated progeny of 'Dahliatown Orchid'.

*Pollen parent*.—Unnamed seedling resulting from multiple crossings of *Hibiscus coccineus* and *Hibiscus moscheutos*.

Origin: A selected seedling from the stated cross.
Type of plant: Hardy, herbaceous perennial.
Classification: Hybrid Hibiscus plant.
Propagation: Relatively easy to propagate; fast rooting; holds its distinguishing characteristics through successive propagations by cuttings and division.
Size: About 3 to 3½ feet tall; about 2½ to 3 feet wide.
Form: Symmetrical annual growth from perennial roots. Plant reaches a mature size (height and spread) in 2 years.
Habit: Upright and uniformly branched.
Growth: Vigorous; medium and compact.
Hardiness: Hardy to at least -30 degrees Fahrenheit. Heat tolerant to about 110 degrees Fahrenheit.
General Health: Plant is highly resistant to fungal diseases; highly resistant to pests such as Japanese beetle, white flies, aphids and spider mites; sturdy through excessive drought or water.
Foliage:
1. *Arrangement*.—Alternate.
2. *Shape*.—Juvenile — variable, 3 to 5-lobed palmate leaf. Mature — refined, palmate to hastate 3 to 5 lobed leaf with relatively smooth margins with some serrations, acute apices, rounded to cordate base.
3. *Size*.—Mature leaf — (petiole base to apex) length is about 5¾ inches (14.5 cm), width is about 4 inches (10 cm).
4. *Color*.—Young leaves (upper side) — 11-L page 119 ,PLATE 48. Mature leaves — (upper side) — 12-L, page 119, PLATE 48; background green — 4-L, page 69, PLATE 23. Veins — 6-J, page 37, PLATE 7. Underside of mature leaves — 3-H, page 37, PLATE 7.
5. *Surface texture*.—Glabrous with some luster.
6. *Petiole length*.—About 2½ inches (5.5 cm).
7. *Petiole color*.—Slightly brighter than 6-J, page 37, PLATE 7.

Stems: The stems are stout at the base, becoming more slender toward the apices; coloration is similar to the petiole.

THE FLOWER

Blooming period: Profuse from July until frost.
Flower diameter: Large; about 7 inches (18 cm).
Borne: Singly in leaf axils, from midpoint of stems upward.
Bloom duration: Individual bloom lasts at least one full day. Typically, the plant exhibits from 25 to 40 blooms at a time under landscape conditions.
Form: Campanulate; 5 petals; petals are also very overlapping.
Bud:
1. *Length/Shape/Diameter*.—Oblong, Diameter about 1 to 1½ inches; Length about 1½ inches (4 cm), on day before opening.
2. *Color*.—12-A, page 135, PLATE 56.
3. *Surface texture*.—Glabrous.
4. *Duration*.—One to two weeks.

Corolla:
1. *Petal character and dimensions*.—Campanulate and very overlapping. Length is about 4½ inches (12 cm). Width is about 4½ inches (12 cm).
2. *Coloration*.—Plum with purple center or eye (about 2½ inches (5½ cm) and purple streaking extending outward from eye to edges of petals; eyezone is very glabrous. (a) Plum petals — 2-K, page 113, PLATE 45. (b) Venation in petals — Closest to 12-L, page 133, PLATE 55. (c) Eye zone — Between 12-L, page 133, PLATE 55 and 12-A, page 135, PLATE 56.
3. *Texture*.—Smooth.
4. *Substance*.—Thick.
5. *Shape*.—Campanulate and very overlapping.

Reproductive organs:
1. *Staminal column*.—Stamen along basal two-thirds. Stamen length — About 1 inch (3 cm). Stamen color — Between 4-A, page 29, PLATE 3 and 1-B, page 29, PLATE 3. Pollen color — 3-K, page 41, PLATE 9.
2. *Style*.—Terminates upper one-third of Staminal column. Stigmatic lobe color — Bright version of 6-K, page 35, PLATE 6.

Calyx: Connate at the base; about 1½ inch (3 cm). length.
Stipules: None
Epicalyx: Whorl of bracts.
1. *Shape*.—7–10 slender, sword-shaped bractlets.
2. *Length*.—About ¾ inch (2 cm).
3. *Color*.—1-L, page 53, PLATE 15; tips — 6-L, page 39, PLATE 8.

Peduncle:
1. *Length*.—About ½ inch (1½ cm).
2. *Strength*.—Stiff and sturdy.

Fruit/seed: Seed set is minimal. Round seeds, about 1 cm in diameter, appear in rows inside of a rounded pod.

GENERAL OBSERATIONS

This plant, as a hybridized hardy Hibiscus, is valuable to the landscape market for its improvements in thicker textured and uniquely colored and shaped flowers, refined "maple-cut", dark plum-purple colored foliage, all-around vigor, compact conical habit, and adaptation to extreme environments, including the ability to consistently survive winter temperatures of at least −30 degrees Fahrenheit.

We claim:

1. A new and distinct cultivar of hibiscus plant, as herein shown and described, characterized by its dark, rich, purple "maple-cut" foliage, its large, cup-shaped plum flowers with dark purple centers and purple streaking to the petal edges, its vigor, and its hardiness.

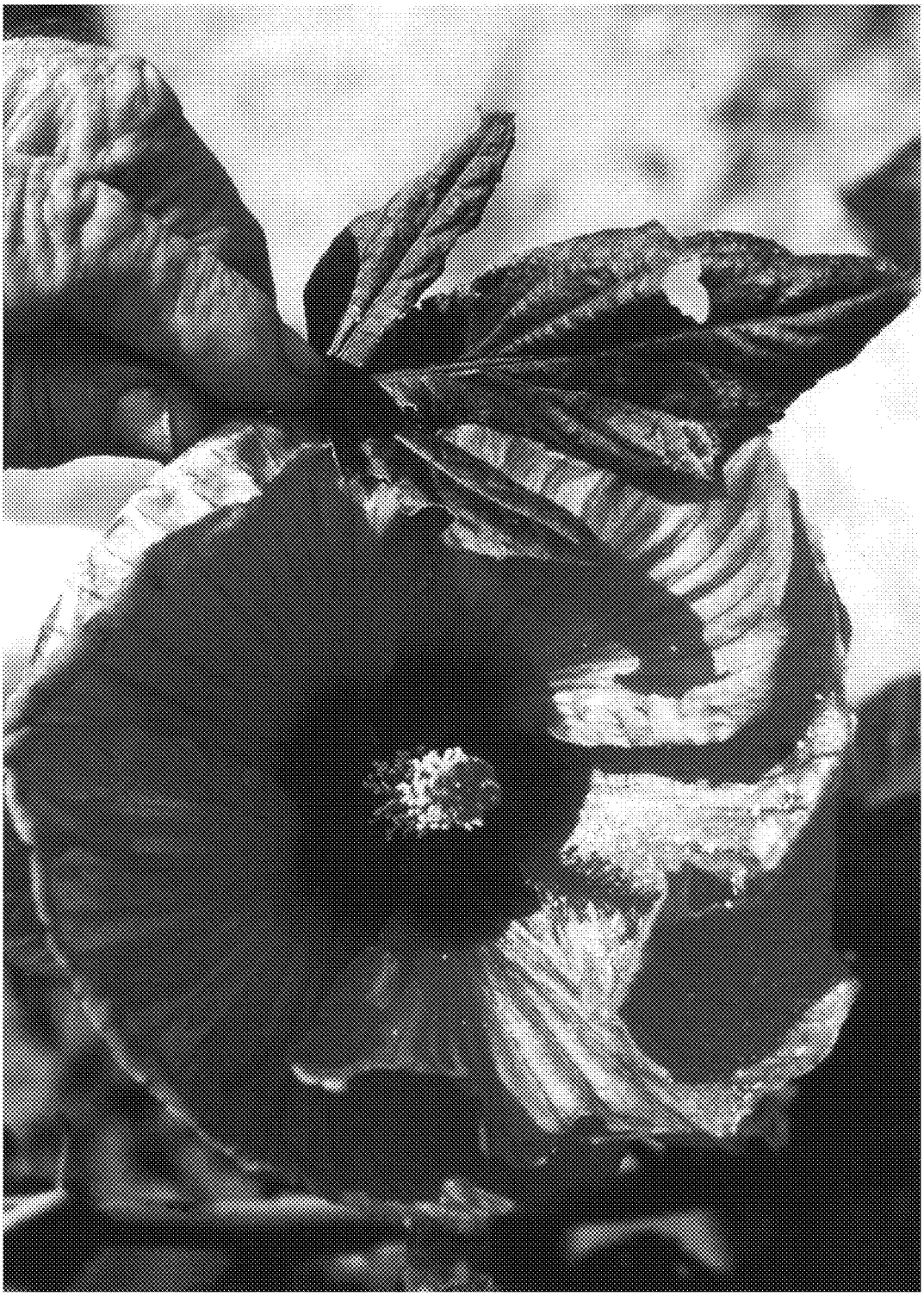

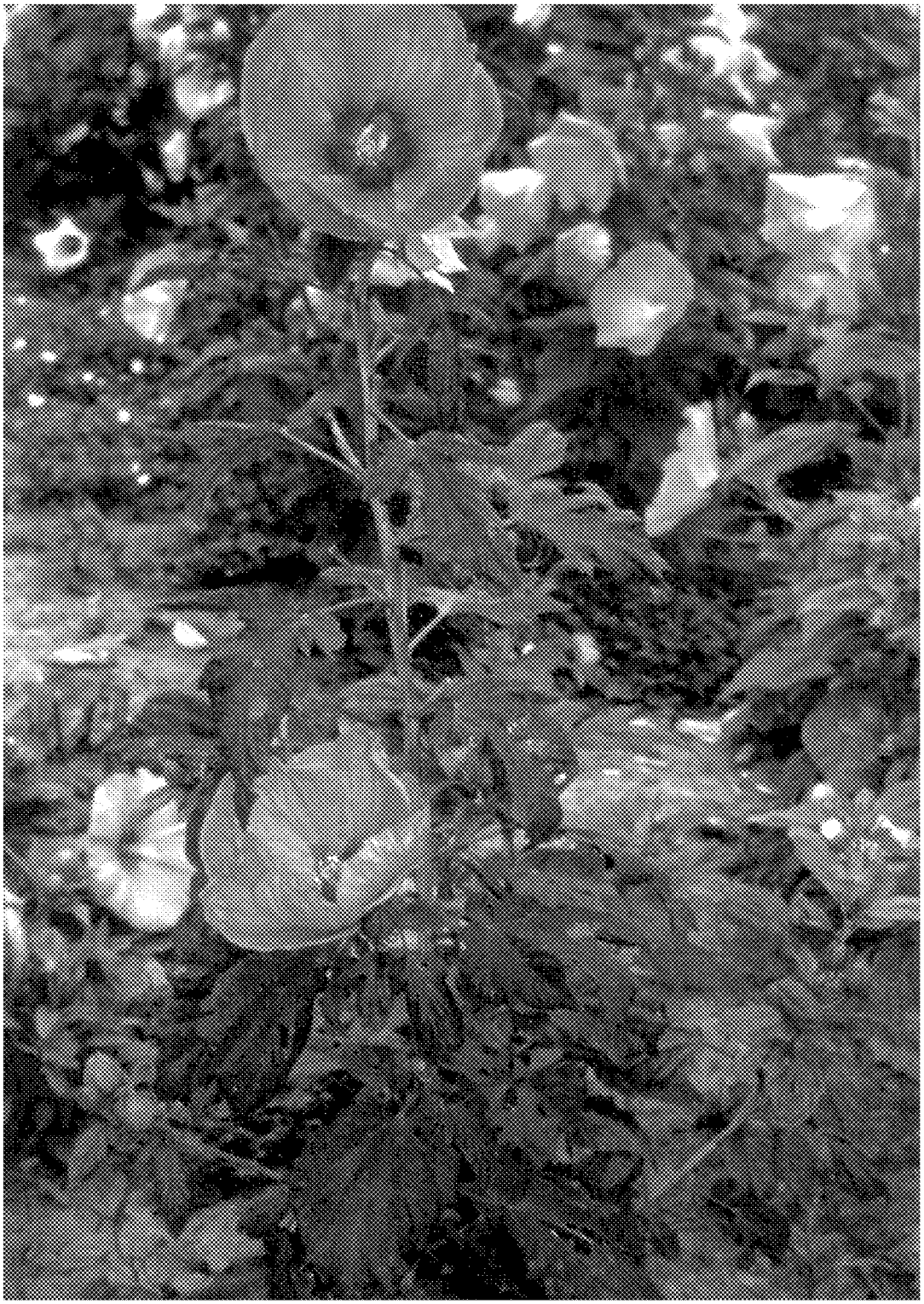

* * * * *